United States Patent [19]
Antons et al.

[11] Patent Number: 4,978,296
[45] Date of Patent: * Dec. 18, 1990

[54] DISPOSABLE TOOTH COLOR SHADE GUIDE

[76] Inventors: Peter Antons; Samra L. Antons, both of 2 Oak Grove, both of Irvine, Calif. 92714

[*] Notice: The portion of the term of this patent subsequent to Apr. 24, 2006 has been disclaimed.

[21] Appl. No.: 432,203

[22] Filed: Nov. 6, 1989

Related U.S. Application Data

[63] Continuation-in-part of Ser. No. 334,364, Apr. 7, 1989, Pat. No. 4,919,617.

[51] Int. Cl.$^5$ .............................................. A61C 19/10
[52] U.S. Cl. ...................................................... 433/26
[58] Field of Search ................... 433/26; 206/63.5, 83; 604/361; 116/206, 207

[56] References Cited

U.S. PATENT DOCUMENTS 2,156,880  5/1939  Slomon ............................... 604/361
4,292,916  10/1981  Bradley et al. ...................... 116/207

Primary Examiner—Cary E. Stone
Attorney, Agent, or Firm—Gordon K. Anderson

[57] ABSTRACT

A tooth color shade guide which has a body (20) constructed from photographic paper, thermoplastic, or cardboard, having a number of fingers (22) distending from a base portion (28). A specimen (32) of a color shade is located on the end of each finger, each having a different hue and alpha-numeric designations (34) adjacent thereunto allow natural tooth color to be matched and identified. The attaching end (26) of the fingers are perforated (30), permitting them to be individually torn-off for comparison and then the entire color shade guide may be disposed of after use. A visual indicating surface (38) may be added to the fingers that is light sensitive and changes color in a few minutes after exposure. This surface (38) has a message imprinted in writing indicating the guide has been used preventing cross-contamination with other patients. Alternately, a moisture indicating surface (39) may be added to the back of each finger exhibiting use by changing color when in contact with moisture present in a persons mouth.

6 Claims, 1 Drawing Sheet

DISPOSABLE TOOTH COLOR SHADE GUIDE

RELATED APPLICATION

This application is a continuation-in-part of application Ser. No. 07/334,364 filed Apr. 7, 1989, now U.S. Pat. No. 4,919,617.

TECHNICAL FIELD

The present invention relates to dental color shade guides in general, and more specifically to a set of shade guides that are individually removable with the entire set disposed of after use.

BACKGROUND ART

Previously, many types of color shade guides have been in use allowing the dental practitioner to match the color of a patients tooth and communicate the color to the manufacturer, fabricating a restoration. In the past, a number of color samples have been attached to either a fixed, rotatably separate metal plate or an artificial tooth, or portion thereof, attached to a separable holder. In any event, the dentist positions the color sample on or near the tooth being restored in order to visually ascertain and classify the color of the natural tooth. In most cases, prior art has reproduced a tooth in basic shape and size, even to the extent that the entire exposed surface of the tooth has been formed and a handle member is attached to allow manipulation. Further, some devices utilize pivot connections between the specimen and the handle, allowing convenient positioning in the oral cavity.

A search of the prior art did not disclose any patents that read directly on the claims of the instant invention, however, the following U.S. patents were considered related:

| U.S. Pat. No. | Inventor | Filing Date |
| --- | --- | --- |
| 4,620,841 | Farrell et al | Dec. 24, 1984 |
| 4,541,801 | Rodenbach et al | Apr. 13, 1984 |
| 4,207,678 | Jeannette | Sep. 26, 1977 |
| 4,115,922 | Alderman | Sep. 20, 1976 |
| 3,964,167 | Yerkes | Oct. 24, 1974 |
| 3,378,925 | Faller | Jul. 14, 1965 |
| 2,805,478 | Adams | Jan. 20, 1955 |

Farrell et al teach a metal blank with metal bars covered with dental glass fused onto a layer of different colored opaque material with a clear glaze on the top. The shade guide is configured as a single element with individual colors in a contiguous arcuate fan-like array allowing the guide to be held and the particular shade matched to the material tooth by the position maintained.

Rodenbach discloses a number of removable color rods for color comparison. The rods project from a frame and a stud snaps into a bore holding it in place in this frame. The rods are positioned side by side and are individually removed for use. The rod does not have the shape of the tooth, instead is rectangular, the same width as the balance of the rod.

Jeannette similarly provides a holder for guides stored side by side. The individual guides have either a specific chroma percentage or a primary shade. In use, a primary color is selected which matches most closely the patients natural teeth. A set of secondary shade guides correspond to the primary, except they contain a selected chroma percentage defined by a predetermined value ratio achieved by a color modifier allowing selection of the nearest color by comparison. The color specimens are in somewhat the shape of a tooth and have a handle on the opposite end.

Alderman teaches a shading system with both gingival and incisal shade selectors with the holder hinged in the middle. Shade buttons of the gingival selectors are concave, tapering to a thin edge and the incisal selectors are convex and relatively thicker. Each selector is removable from the hinged case.

Yerkes utilizes a disposable tooth shade guide with a tooth simulating member much the same shape as a tooth. A mounting member pivotally holds the tooth and a translucent cover alters the color by having different color variations producing a combined color. The cover may be removed and discarded after use.

Faller's approach to the problem of sanitation uses a tank filled with disinfectant in which the shade guide is immersed. A support, in the form of a lid having a center wall member with slots on each side, secure individual elements. The slot is outwardly tapered to hold the individual elements in place.

Adams pivots a set of artificial teeth of different hues in a holder allowing a desired number of teeth to be selectively positioned adjacent to the oral cavity of a patient. The non-required teeth may be moved laterally away and supported in that position while the comparison is being made.

It is very apparent that the prior art has limited its attention to guides that are maintained in sets either connected together and pivoted or individual samples capable of being selected for comparison and thereafter stored in a convenient container. Nowhere has a truly economically feasible, disposable guide been employed.

DISCLOSURE OF THE INVENTION

With this prior art in mind, the basic problem has been solved, that of duplicating colors of natural teeth for restorations. This art has developed to such an extent that industry standard designations are used representing each color. The dentist makes the selection and provides the manufacturer with the alpha-numeric reference for the color, which is jointly recognized by both parties.

While this practice and the prior art has been in existance for some time, society, at least in this and more developed countries, has become much more concerned with health and hygiene, particularly toward prevention of contracting a communicable disease. The apparent need has, therefore, arisen for a device to accomplish the color comparison without having to be used by more than one person. Since prior art employs rather expensive simulated teeth or sample chips on pivoting handles, and the like, it would be economically impracticle to use such an array of colors in a set and then dispose of them entirely.

It is, therefore, a primary object of the invention to provide a disposable color shade guide that contains all of the normal colors in a convenient row with the capability of simply tearing off one or more samples and actually touching the tooth allowing comparison with teeth on both sides. This is accomplished by utilizing a thin material with the colors in linear array grouped in logical sequence, each positioned on the ends of a series of fingers that are easily removed by tearing a perforated portion. This allows the dentist to tear off the sample and position it properly on the teeth and then dispose of it and the remaining guide when the selection is made. The advantage of this system is obvious in that no cross-contamination may occur between patients nor with the person using the guide. Great care and expense is presently being incurred by individuals and government regulatory agencies to prevent the spread of disease, particularly in the medical and dental field.

An important object of the invention is directed to the configuration of the guide, as it is very thin and yet has enough body to be handled easily. This slenderness allows the color specimen to be positioned on the same plane as the adjoining teeth and, as the shape is toothlike and similar is size, optical aberations are nearly eliminated. Prior art use, in many cases, an actual toothlike sample that is close to the same thickness as a tooth. Some of these samples pivot using a handle on the back requiring considerable depth and placing the actual sample well above the other teeth. In either case, comparison is difficult and subject to different light deflections, due to the height variations. The inventions improvement in configuration alone is indeed novel and unique from this standpoint.

Another object of the invention is the addition of a black outline around the outside edge of the color specimen. While this may appear insignificant on the surface in practice the outline adds considerably distinction in matching the color of the natural tooth. While prior art completely lacks this feature, its presence allows the comparitor a clear graphic perception of the color differential or similarity as the two colors are disassociated by the thin opaque outline. The actual advantage must be physically observed to be fully appreciated.

Still another object of the invention is the ability to mass produce the device in such quantities as to be economically feasible, sufficient to be completely discarded after use. This object is realized by reproducing the invention by photography, holography, lasers, or other similar processes on a thin relatively inexpensive material, such as paper, cardboard, thermoplastic sheets, and the like. Today industrial advancement allows a wide variety of reproduction techniques that are cost effective. Die cutting tooling using small punch presses are common in the industry and basically inexpensive, particularly when the cost is amortized over a large quantity of product. This invention, therefore, uses the latest production methods to the best advantage, making the device inexpensive enough to be easily discarded after use, with little consideration given by the dental practitioner in the overall cost of his or her services.

Yet another object of the invention allows visual indication of actual use preventing completely potential contamination from one patient to another. Over and above the fact that the finger with the color specimen is torn-off during use, either photo-chemical light sensitive printing or a moisture indicating surface is applied to the color shade guide that actually appears when exposed to light or changes color characteristics when subjected to moisture. A warning is printed on the finger that appears a short time after it is exposed to light or the latter surface may be made of a litmus coating or similar material that, in the presence of saliva in the mouth or even the moisture on the dentists fingers, changes the color according to the acid or alkalin content in the liquid making a visible display apparent.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
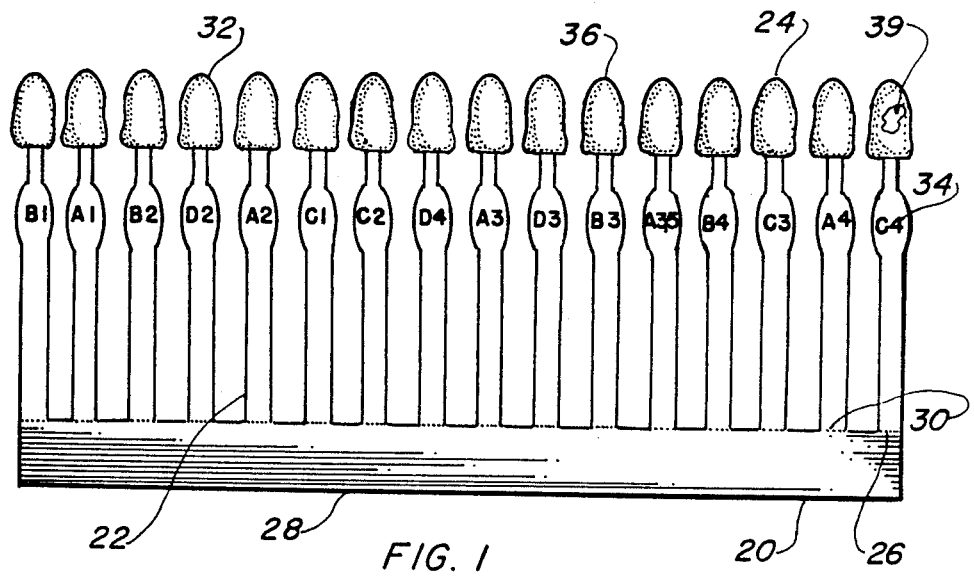
FIG. 1 is a plan view of the preferred embodiment.
Figure 2:
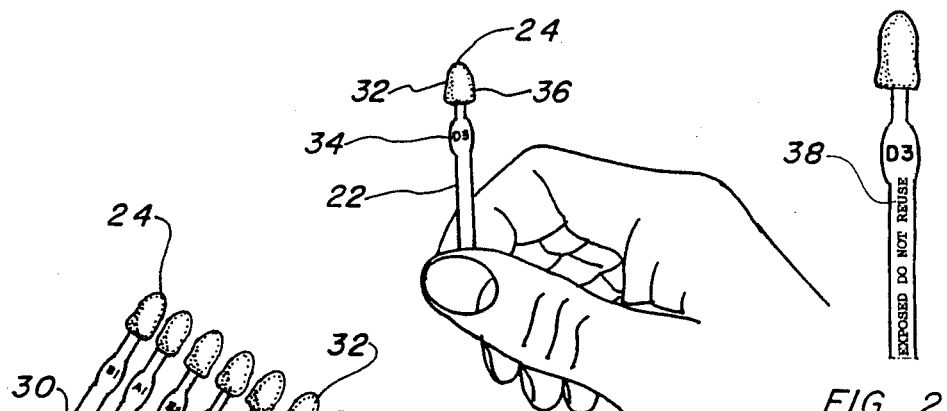
FIG. 2 is a plan view of a separate finger removed from the shade guide illustrating the imprinted lexical form that has changed color and is visible.
Figure 3:
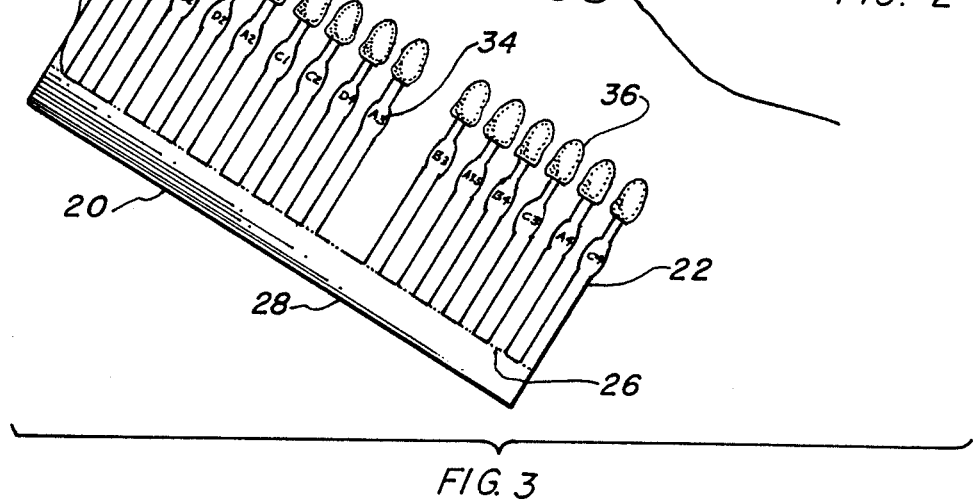
FIG. 3 is a partial isometric view of the preferred embodiment with a separate finger containing the color specimen torn-off of the shade guide and held in the normal manner for use.

The best mode for carrying out the invention is presented in terms of a preferred embodiment. The preferred embodiment, as shown in FIGS. 1 and 2, is comprised of a flat thin body 20 with a front side and a back side. The body 20 is die cut to form a number of separate fingers 22 making them integral with the body. The fingers 22 are longer than they are wide creating a straight, slender portion most of the length terminating at an extended end 24. An attaching end 26, which is the other end of the finger, is connected to a base portion 28, also integral with the body. The interface maintains communication, however, a plurality of holes in the form of perforations 30 divide the base 28 from the fingers 22. This arrangement of aligned holes allows the fingers to be easily detached by tearing from the base, as illustrated in FIGS. 2, and then used individually, much like removing paper matches from a match book.

On the extended end 24 of each finger 22 a color shade specimen 32 is provided in the shape and form of a human incisor tooth. Each finger specimen 32 contains a different hue, preferably starting from the lightest to the darkest in descending order from left to right. The specimens 32 are graded to an industry standard that match the majority of human teeth, allowing the user to match exactly, or within an acceptable tolerance, most teeth that are being restored or replaced.

To permit an accurate color contrast, an opaque outline 36 is added on the periphery of the color specimen 32. This outline 36 may be any color, however, black is preferred which distinctly defines the actual contrast between the natural tooth and the color shade specimen 32. This novel arrangement is far different than prior arts three dimensional tooth, as it allows the user to compare the colors from an objective viewpoint, as distinction is easily made between the two colors being equated. This outline 36 is relatively small, about the width of the boundary, as shown in FIG. 1, and as the specimen is cut from the parent body 20 the outline would appear as a line approximately a pen or pencil line thick, just enough to differentiate and contrast the specimen 32 from the tooth.

In order for the color of the specimen 32 to be identified, indica in the form of an alpha-numeric designation 34 is assigned which is used almost universally in the industry. This designation 34 is placed on each finger 22 below the specimen 32 in an area preferably wider than the finger itself. The actual location is not limited to this area, but must be convenient to the user for easy recognition. FIG. 1 illustrates the preferred location and the designations 34 commonly in use.

The body 20, which includes the fingers 22 and base portion 28, may be made of a number of basic materials, such as photographic print paper on which a photograph has been reproduced, accurately duplicating the colors of the specimen 32 clearly and easily, also replicating the designations 34. The material may also be a thermoplastic sheet using the same photographic process or a thin layer of paint reproducing the colors. The body 20 may further be formed on paper or cardboard with the specimen 32 and indica 34 deposited by printing with ink or paint. Further, a lamination of any of the above substances may be utilized with adhesive or heat sealing creating a bond therebetween. In order to enhance the color and improve the image of the specimen 32 a hologram may be used with the image holograghly printed using means well known in the art. Further, the specimen 32, as well as the entire body 20 may use laser printing techniques that are presently coming into common usage in the printing industry. It will be noted that the materials and printing procedures are certainly not limited to those described above, as any suitable composition may be used with equal ease provided that the color is not effected.

In order to prevent cross-contamination or exposure of disease from the patient to the dental practitioner, a visual or moisture indicating surface may be added to the finger 22. The preferred visual surface 38 consists of a photo-chemical light sensitive ink that is imprinted in lexical form on either the front or back of the finger 22. The printing carries the warning in the written language of the user, such as in english, the terms "consumed", "exposed", "used", "do not reuse" with "exposed do not reuse" preferred, however, other similar words may be used with equal clarity. FIG. 2 illustrates the preferred printed form for the english language. The preferred material is a formulation of silver based light sensitive ink that changes from a light color that blends with the background to a distinctive graybeige color that becomes visible after a few minutes when exposed to ordinary light, either natural or artificial. The particular ink is formulated to be used with the printing process and the sensitivity to light may be adjusted to obtain the desired time duration for visibility. It has been found that light sensitive ink, formulation number 4810, manufactured by TEM TEC, INC. of Spring Valley, N.Y., is ideal for use with the color guide and changes color within a very few minutes after exposure, making the words easily identifiable to the user. The moisture indicating surface 39 may be a type of chemical or composition that creates a change in appearance when subjected to moisture. A litmus coating is one such material that reacts to the acid content in the moisture by turning the color red and an alkali by changing to a blue color. It is understood that when the finger 22 touches the patients tooth or dentists finger sufficient moisture in the form of saliva is present making the color change. If the finger 22 does not actually touch the patients teeth, no contamination is present anyway and the fact that the finger is torn away from the base 28 further precludes use with other patients. Since the manufacturing techniques allow the color shade guide to be cost effective, particularly in large quantities, the disposable feature will be obvious and not a consideration even without the visual or moisture indicating surface 38 or 39.

In use, the invention is housed in either a matchbook-like cover, or it may be packaged in individual envelopes, or stacked together in a box where large usage is anticipated.

While the invention has been described in complete detail and pictorially shown in the accompanying drawings, it is not to be limited to such details, since many changes and modifications may be in the invention without departing from the spirit and the scope thereof. Hence, it is described to cover any and all modifications and forms which may come within the language and scope of

What is claimed is: the appended claims.

1. A disposable tooth color shade guide for identifying the industry standard color of teeth comprising:
    (a) a flat thin body having a front and a back;
    (b) at least one finger formed integral with said body each having an extended end and an attached end;
    (c) a base portion, formed integrally with said body, having perforations dividing the base portion from each finger at the attached end, such that each finger may be removed by tearing allowing an individual finger of the guide to be used and discarded thereafter;
    (d) a distinct color shade specimen disposed upon the front extended end of each finger, each specimen having a different hue, severally matching the industry standard for the majority of human teeth;
    (e) an opaque outline on the periphery of each color shade specimen distinctly defining the contrast over the true tooth color;
    (f) indica residing on each finger connotating the customary standard shade of each specimen allowing a tooth to be matched in color when being replaced by a dental prosthesis; and,
    (g) visual indication discreetly positioned on said body appearing within a predetermined time indicating a warning in writing of prior usage of the tooth color shade guide preventing cross-contamination of patients by using the same guide.

2. The color shade guide as recited in claim 1 wherein said visual indication further comprises; an imprinted lexical form visually appearing within a specific time duration providing a written warning that the shade guide has been used.

3. The color shade guide as recited in claim 2 wherein said imprinted lexical form further comprises: a photo-chemical light sensitive ink imprinted with words on said finger that change color within a predetermined period of time after exposure to light.

4. A disposable tooth color shade guide for identifying the industry standard color of teeth comprising:
    (a) a flat thin body of photographic print paper having a front and a back;
    (b) at least one finger formed integral with said body, each having an extended end and an attached end;
    (c) a base portion, formed integrally with said body, having perforations dividing the base portion from each finger at the attached end such that an individual finger may be removed by tearing allowing each finger of the guide to be used and discarded thereafter;
    (d) a distinct color shade specimen photographically reproduced on the front extended end of each finger, each specimen having a different hue severally matching the industry standard for the majority of human teeth;
    (e) an opaque outline photographically reproduced on the periphery of each color shade specimen distinctly defining the contrast over the true tooth color;
    (f) indica photographically reproduced on each finger connotating the customary standard shade of each specimen allowing a tooth to be matched in color when being replaced by a dental prosthesis; and, (g) visual indication discreetly positioned on said body appearing within a predetermined time indicating a warning in writing of prior usage of the tooth color shade guide preventing cross-contamination of patients by using the same guide.

5. The color shade guide as recited in claim 4 wherein said visual indication further comprises; an imprinted lexical form visually appearing within a specific time duration providing a written warning that the shade guide has been used.

6. The color shade guide as recited in claim 5 wherein said imprinted lexical form further comprises; a photochemical light sensitive ink imprinted with words on said finger that change color within a predetermined period of time after exposure to light.

* * * * *